United States Patent [19]

Matsui et al.

[11] 4,425,435

[45] Jan. 10, 1984

[54] CHOLESTEROL OXIDASE AND PROCESS FOR PRODUCING SAME

[75] Inventors: Susumu Matsui, Ootsu; Kazuo Nakajima; Tsutomu Taniguchi, both of Kyoto, all of Japan

[73] Assignee: Takara Shuzo Co., Ltd., Kyoto, Japan

[21] Appl. No.: 333,677

[22] Filed: Dec. 23, 1981

[30] Foreign Application Priority Data

Dec. 26, 1980 [JP] Japan .................................. 55-188919

[51] Int. Cl.$^3$ .......................... C12N 9/04; C12Q 1/60; C12R 1/645

[52] U.S. Cl. .................................... 435/190; 435/911; 435/11

[58] Field of Search ................................ 435/190, 11

[56] References Cited

U.S. PATENT DOCUMENTS 4,003,794  1/1977  Sugiura et al. ...................... 435/190

*Primary Examiner*—Lionel M. Shapiro
*Attorney, Agent, or Firm*—Wenderoth, Lind & Ponack

[57] ABSTRACT

Process for producing cholesterol oxidase by cultivating a strain of the class Basidiomycetes. The oxidase oxidizes cholesterol to form cholest-5-en-3-one and hydrogen peroxide.

13 Claims, 46 Drawing Figures

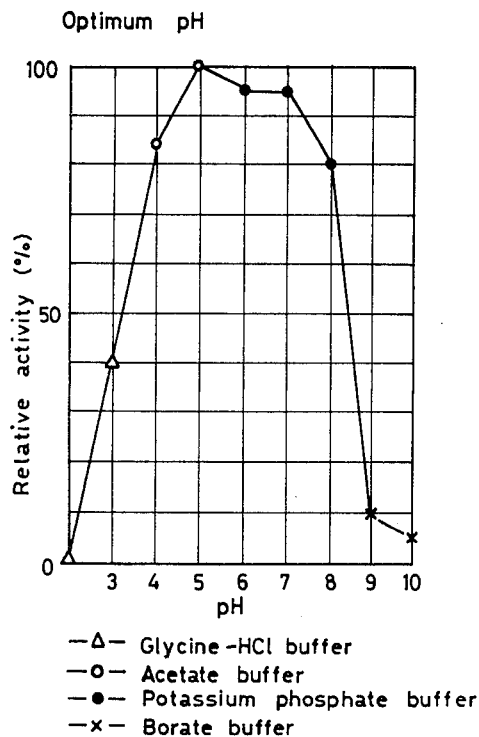
Fig. 1-a
Optimum pH
—△— Glycine-HCl buffer
—○— Acetate buffer
—●— Potassium phosphate buffer
—×— Borate buffer
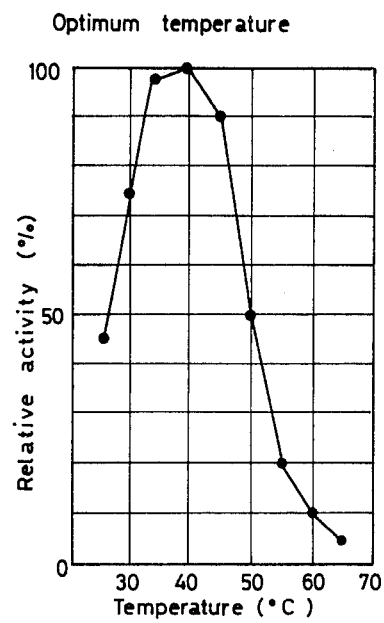
Fig. 2-a
Optimum temperature
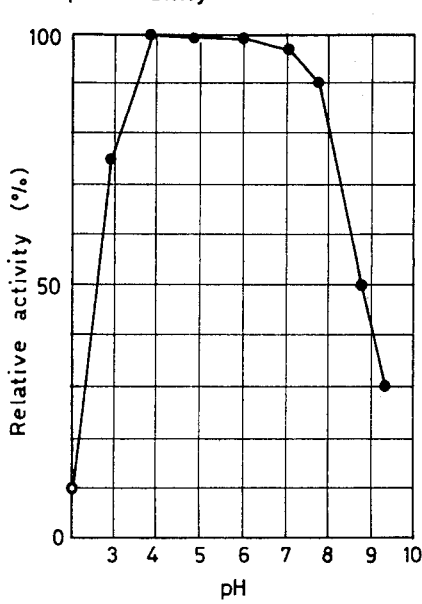
Fig. 3-a
pH stability
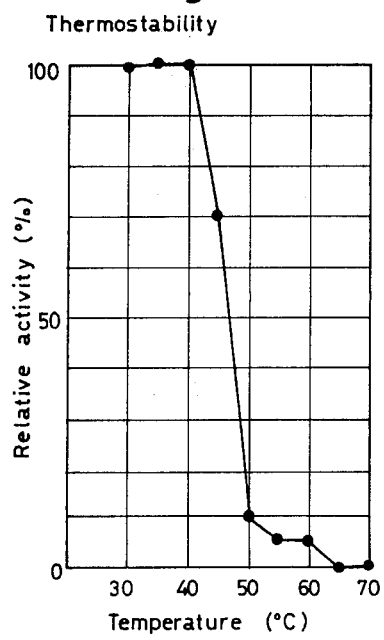
Fig. 4-a
Thermostability

Fig. 1-b
Optimum pH
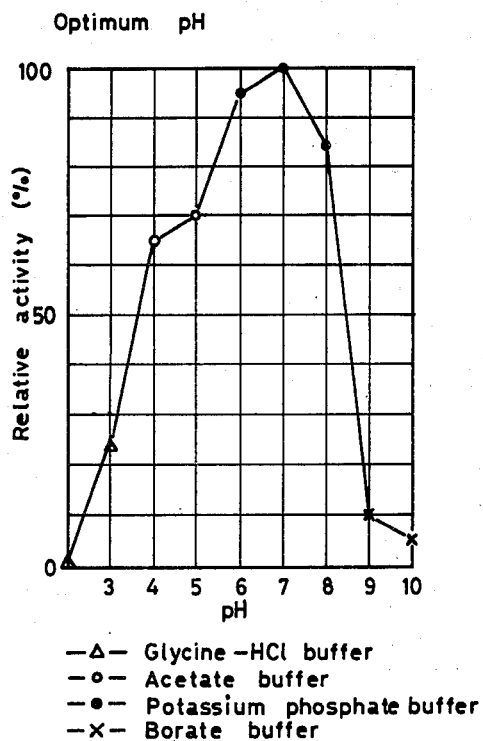
—△— Glycine —HCl buffer
—○— Acetate buffer
—●— Potassium phosphate buffer
—×— Borate buffer
Fig. 2-b
Optimum temperature
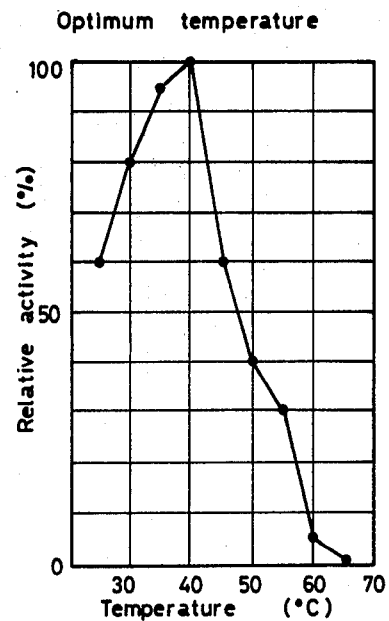
Fig. 3-b
pH stability
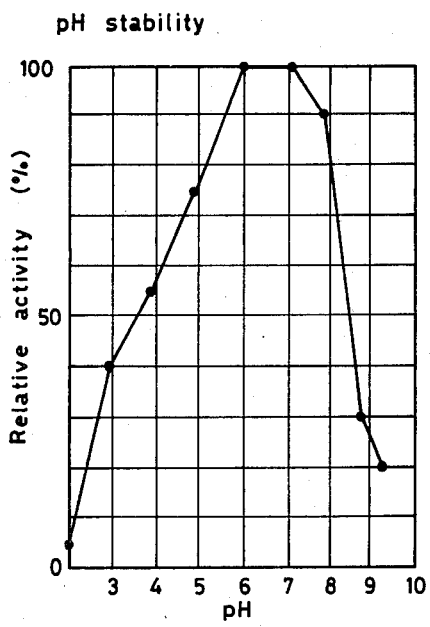
Fig. 4-b
Thermostability
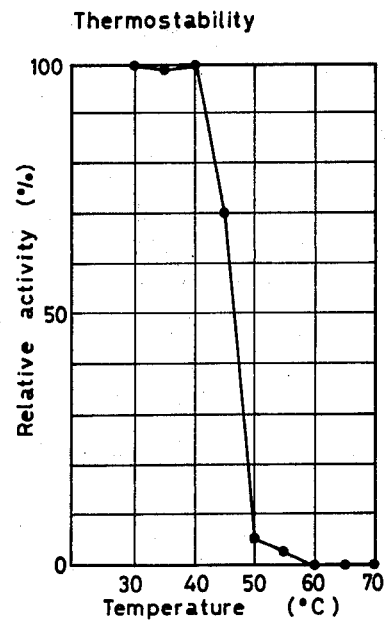

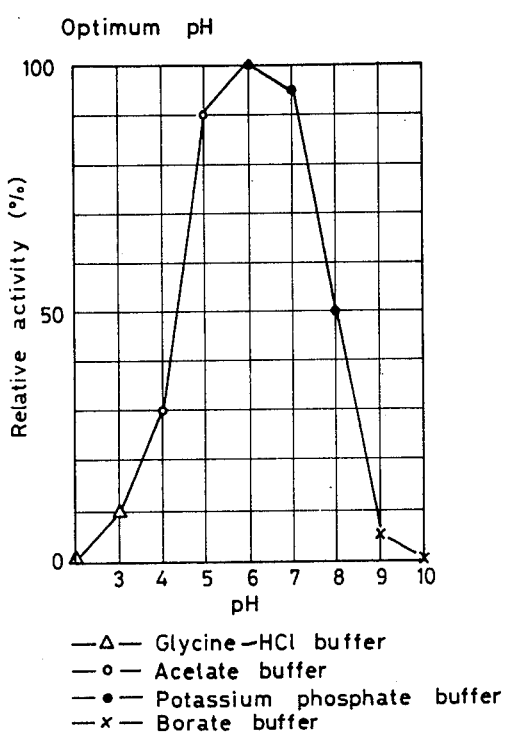
Fig. 1-c
Optimum pH
—△— Glycine—HCl buffer
—○— Acetate buffer
—●— Potassium phosphate buffer
—×— Borate buffer
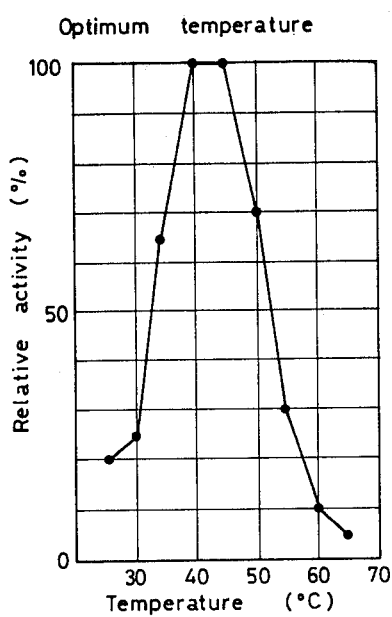
Fig. 2-c
Optimum temperature
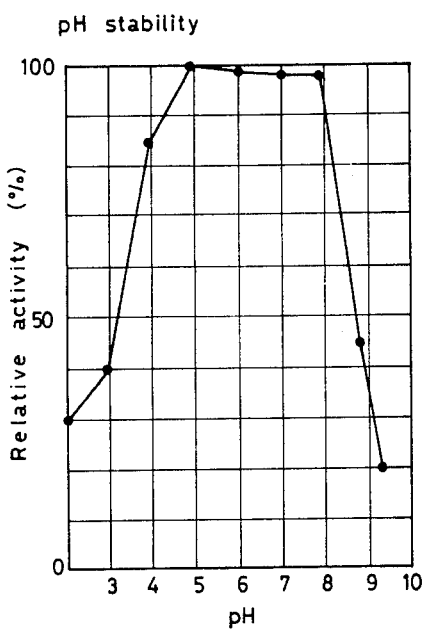
Fig. 3-c
pH stability
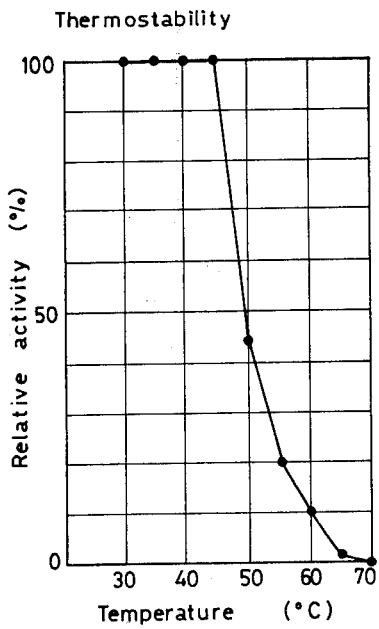
Fig. 4-c
Thermostability

Fig. 1-d
Optimum pH
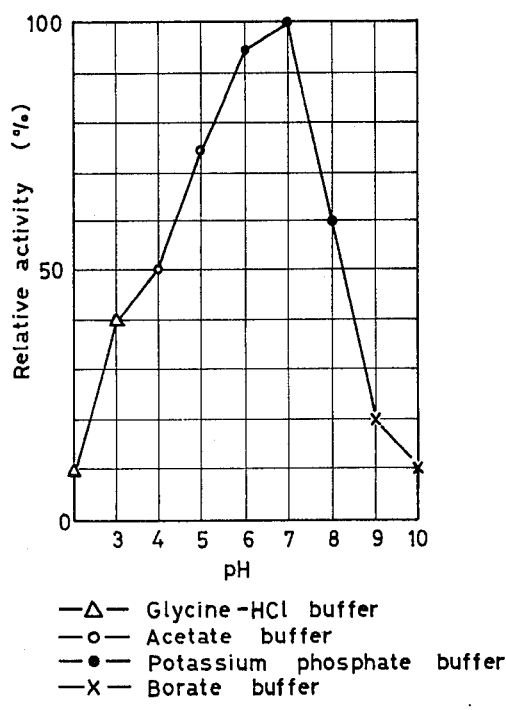
—△— Glycine-HCl buffer
—o— Acetate buffer
—●— Potassium phosphate buffer
—x— Borate buffer
Fig. 2-d
Optimum temperature
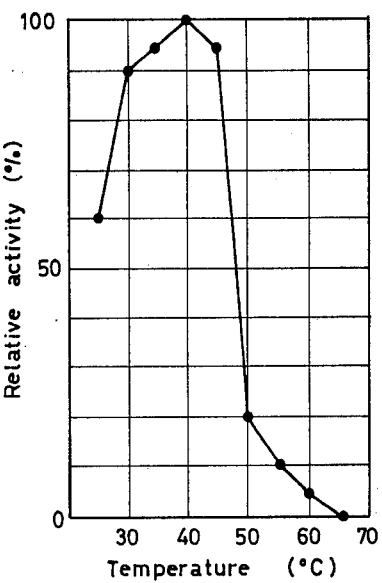
Fig. 3-d
pH stability
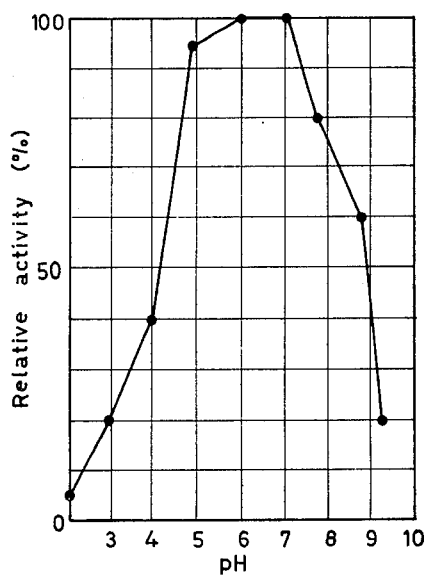
Fig. 4-d
Thermostability
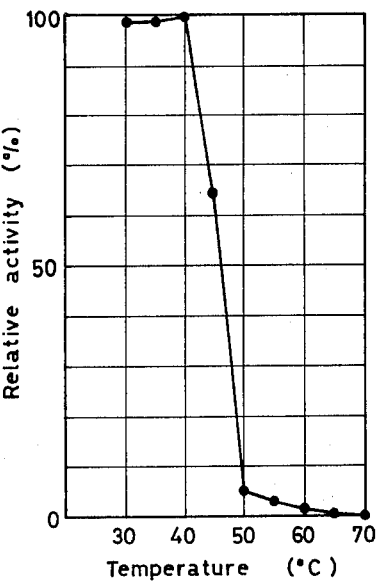

Fig. 1-e
Optimum pH
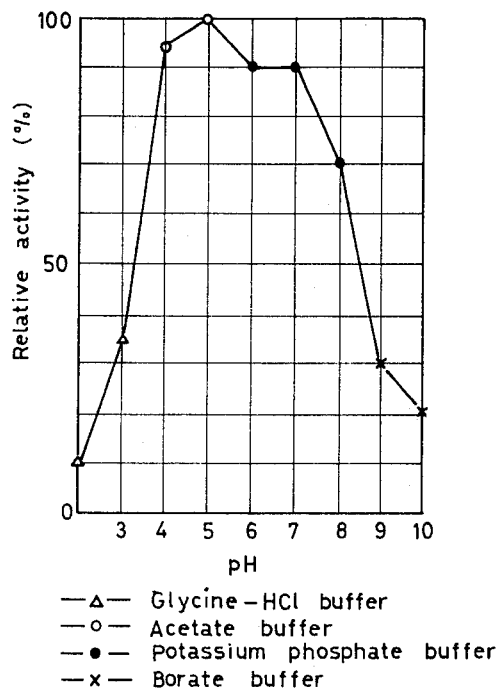
—△— Glycine–HCl buffer
—○— Acetate buffer
—●— Potassium phosphate buffer
—×— Borate buffer
Fig. 2-e
Optimum temperature
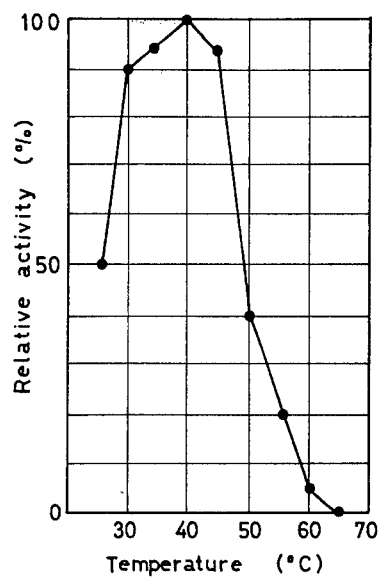
Fig. 3-e
pH stability
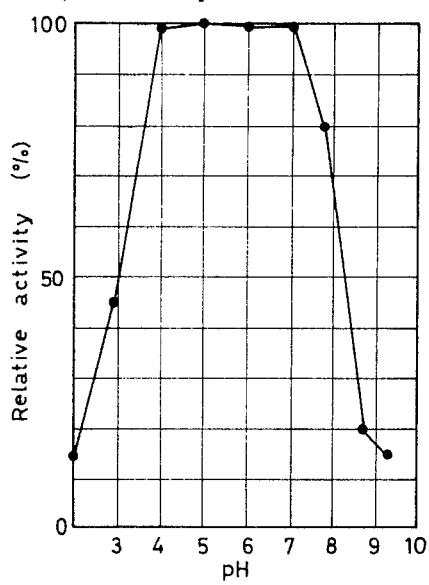
Fig. 4-e
Thermostability
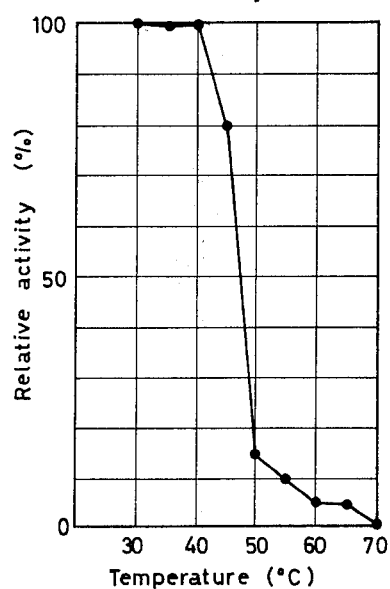

Fig. 1-f
Optimum pH
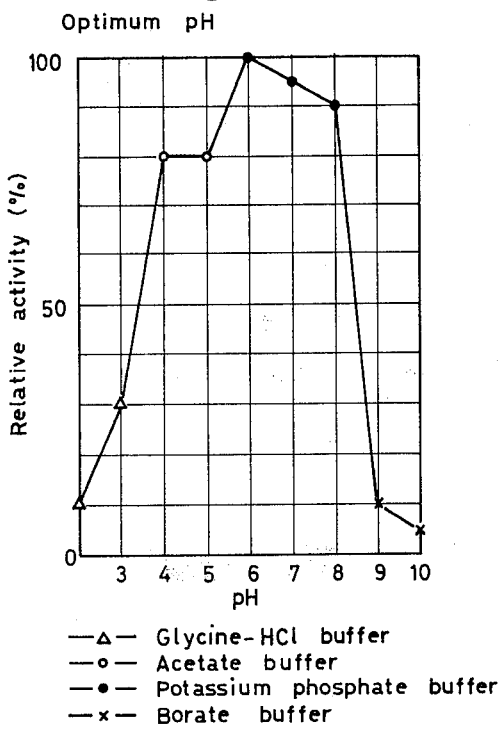
—△— Glycine-HCl buffer
—○— Acetate buffer
—●— Potassium phosphate buffer
—×— Borate buffer
Fig. 2-f
Optimum temperature
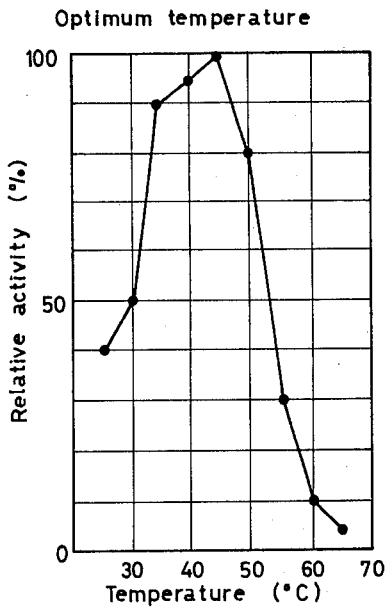
Fig. 3-f
pH stability
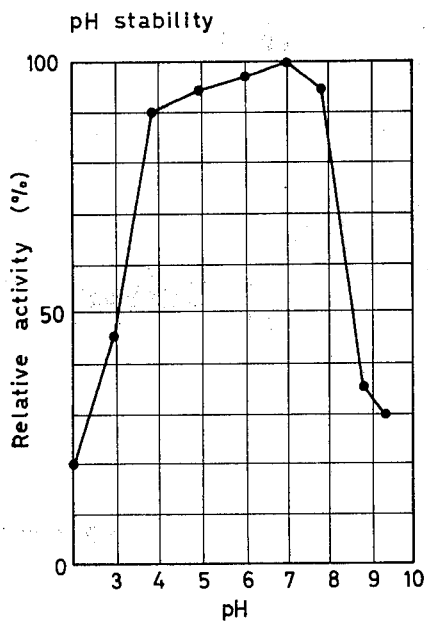
Fig. 4-f
Thermostability
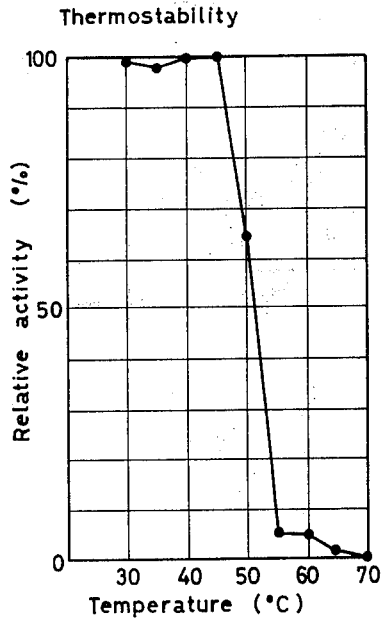

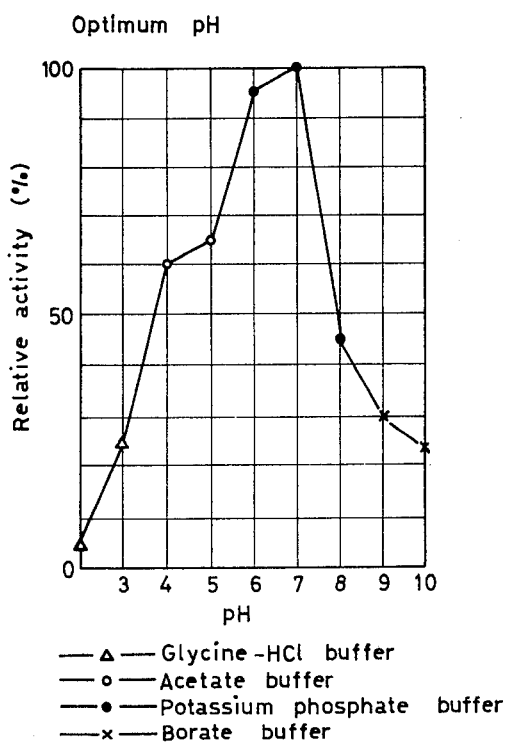
Fig. 1-g
Optimum pH
— △ — Glycine-HCl buffer
— ○ — Acetate buffer
— ● — Potassium phosphate buffer
— × — Borate buffer
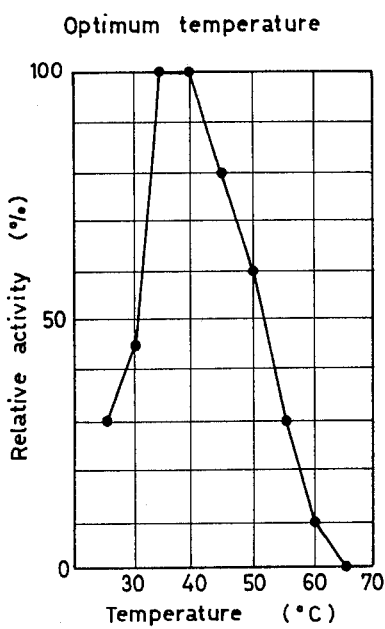
Fig. 2-g
Optimum temperature
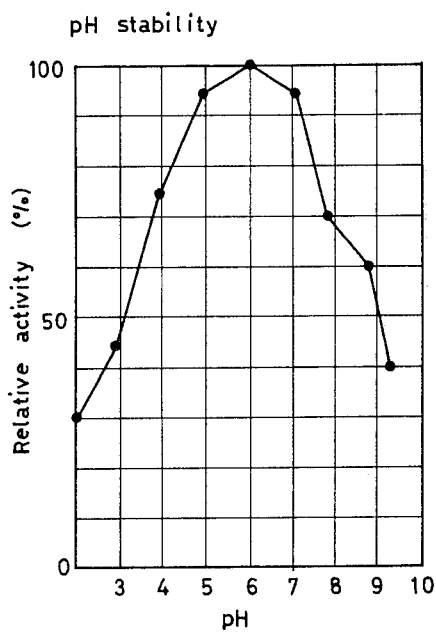
Fig. 3-g
pH stability
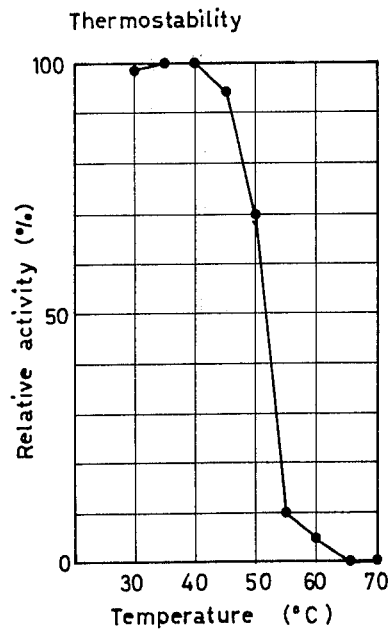
Fig. 4-g
Thermostability Fig. 1-h
Optimum pH
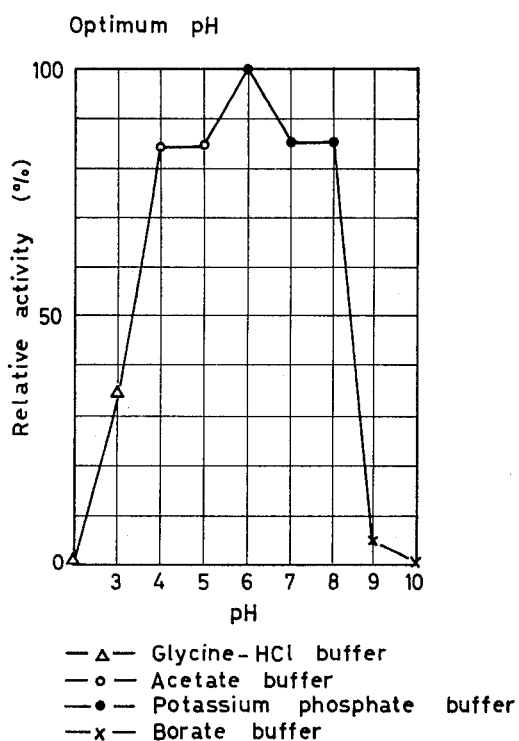
—△— Glycine-HCl buffer
—○— Acetate buffer
—●— Potassium phosphate buffer
—×— Borate buffer
Fig. 2-h
Optimum temperature
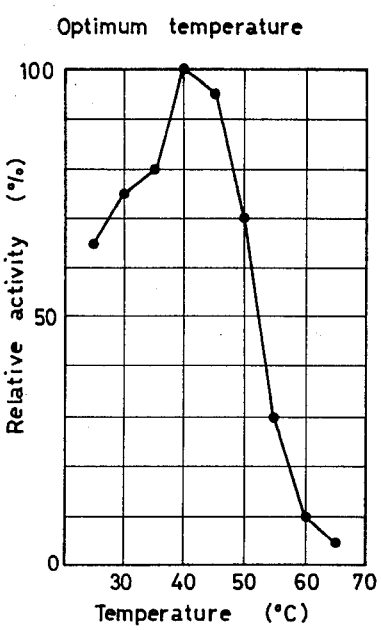
Fig. 3-h
pH stability
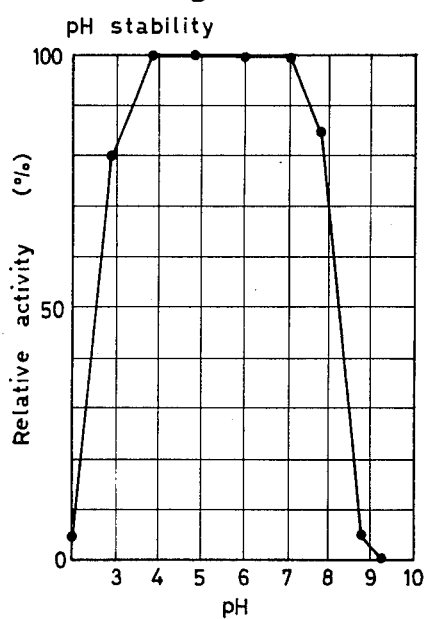
Fig. 4-h
Thermostability
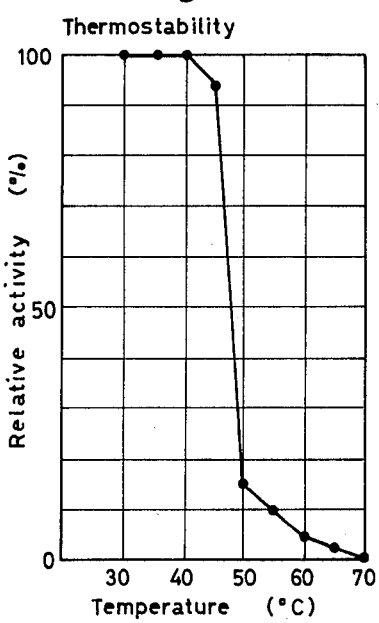

Fig. 1-i
Optimum pH
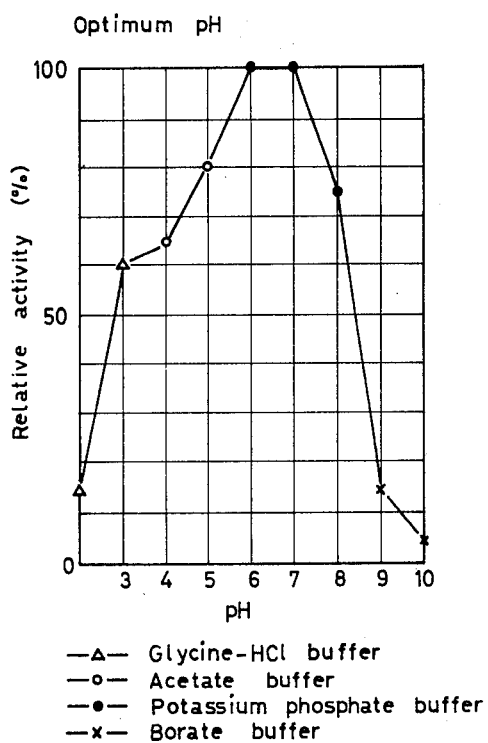
—△— Glycine-HCl buffer
—○— Acetate buffer
—●— Potassium phosphate buffer
—×— Borate buffer
Fig. 2-i
Optimum temperature
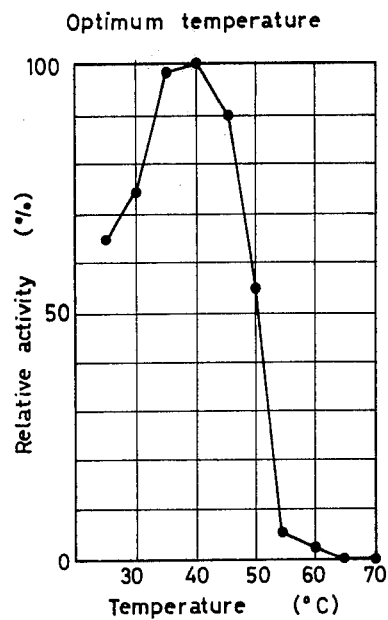
Fig. 3-i
pH stability
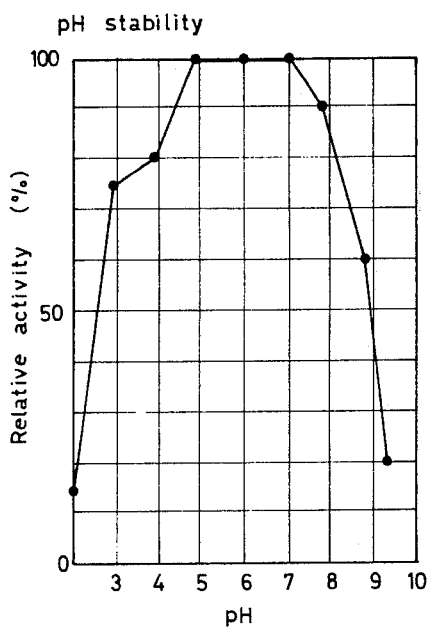
Fig. 4-i
Thermostability
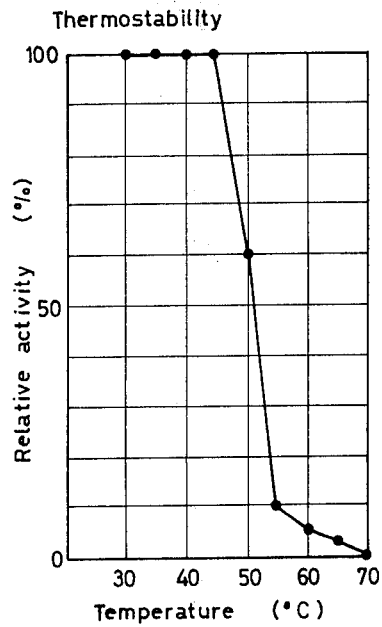

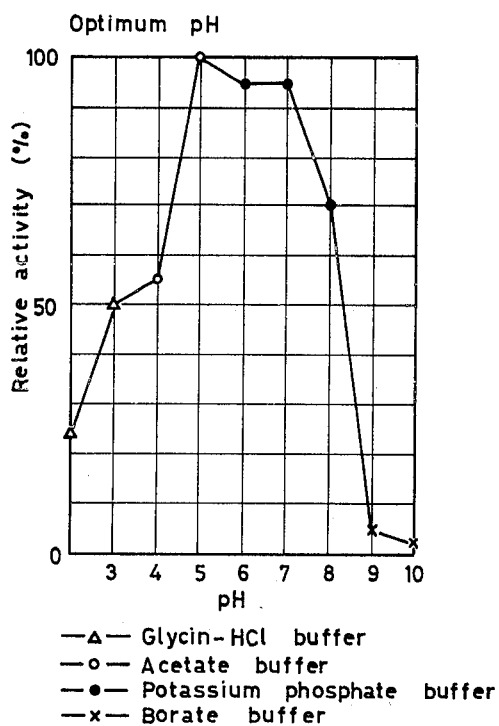
Fig. 1-j
Optimum pH
—△— Glycin-HCl buffer
—○— Acetate buffer
—●— Potassium phosphate buffer
—×— Borate buffer
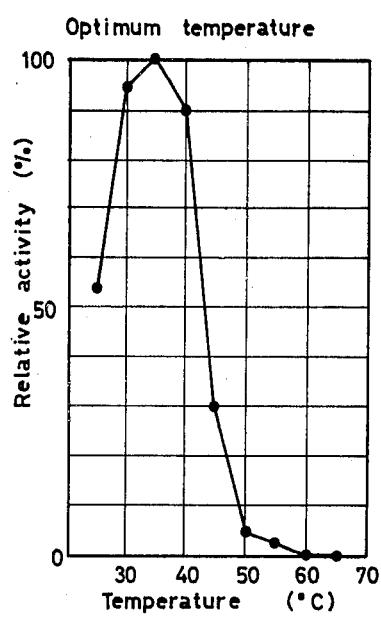
Fig. 2-j
Optimum temperature
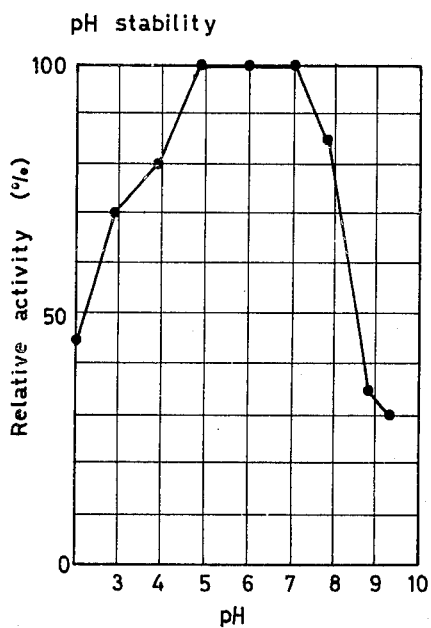
Fig. 3-j
pH stability
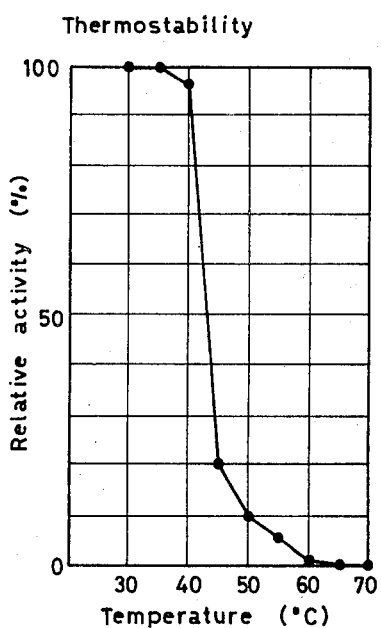
Fig. 4-j
Thermostability

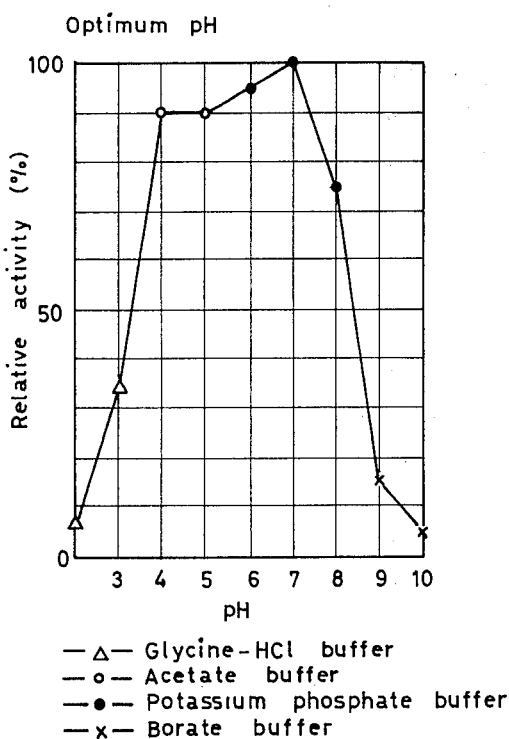
Fig. 1-k Optimum pH
—△— Glycine-HCl buffer
—○— Acetate buffer
—●— Potassium phosphate buffer
—×— Borate buffer
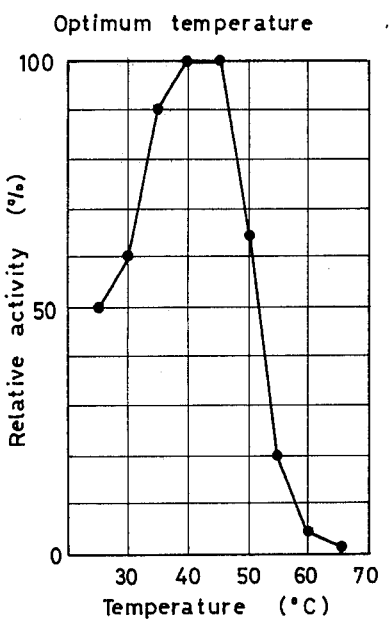
Fig. 2-k Optimum temperature
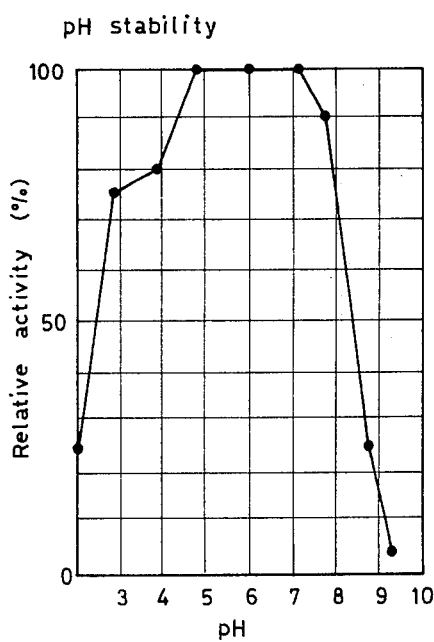
Fig. 3-k pH stability
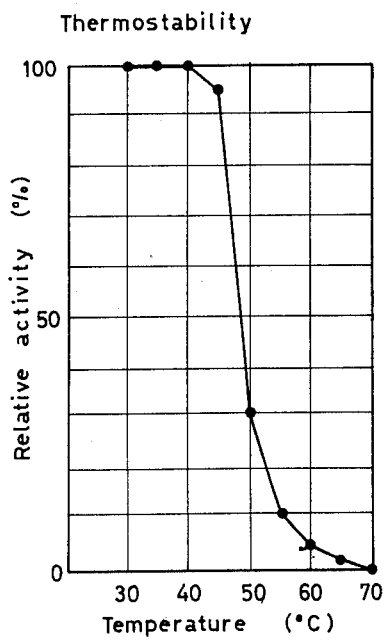
Fig. 4-k Thermostability

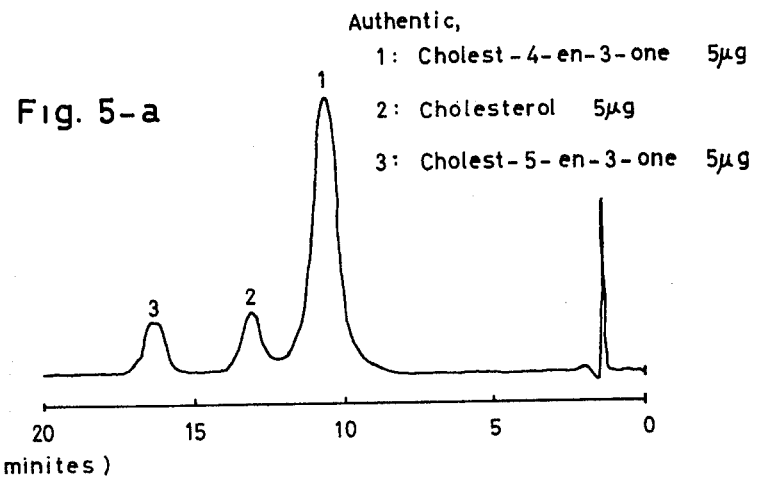
Fig. 5-a
Authentic,
1: Cholest-4-en-3-one  5μg
2: Cholesterol  5μg
3: Cholest-5-en-3-one  5μg
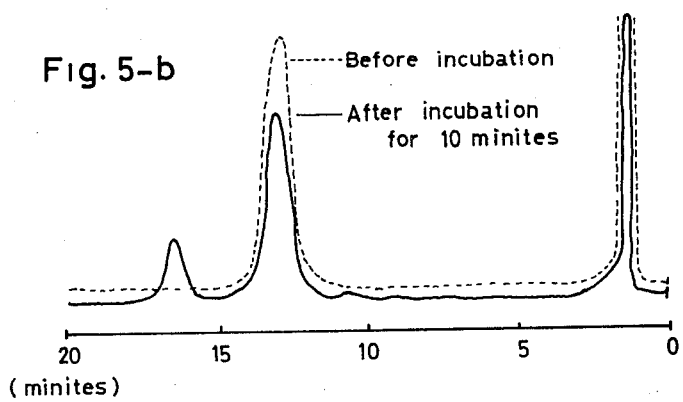
Fig. 5-b
------ Before incubation
——— After incubation for 10 minites
Column: φ40 × 500 mm
Absorbent: μBondapac C₁₈/Corasil
Solvent: methanol:H₂O = 80:20
Flow rate: 0.5 ml/minites
Detector: UV monitor at 210nm

CHOLESTEROL OXIDASE AND PROCESS FOR PRODUCING SAME

This invention relates to new cholesterol oxidase and also to a process for producing the same. More particularly the present invention relates to new cholesterol oxidase which has a high activity towards $\Delta^5$-$3\beta$-hydroxysteroids, particularly high activity to oxidize cholesterol to form cholest-5-en-3-one and hydrogen peroxide, and also relates to a process for producing such new cholesterol oxidase by the cultivation of a strain belonging to the class Basidiomycetes.

In recent years, with the progress of study on the physiological significance of cholesterol in vivo, an increase or decrease of the amount of serum cholesterol has come to be medically regarded as important. For example, it has been found that an extreme increase of serum cholesterol is recognized in cases of arteriosclerosis and cerebral hemorrhage. As a result, an increase of serum cholesterol as detected by its deterimation has come to be utilized for the diagnosis of such diseases as arteriosclerosis and cerebral hemorrhage.

Such determination of serum cholesterol has generally been conducted by a chemical colorimetric method. However the chemical colorimetric method requires a large amount of blood, complicated analytical procedures and a long time to perform. This method, therefore, is undesirable and impractical.

Recently there has been developed for clinical laboratory use for the quantitative determination of serum cholesterol, the so-called enzymatic method, according to which there is utilized a certain cholesterol oxidase (enzyme) which is capable of oxidizing cholesterol in the presence of oxygen to form cholest-4-en-3-one and hydrogen peroxide, which is colorimetrically determined for the quantitative analysis. Thus by the quantitative analysis of so-produced hydrogen peroxide the amount or concentration of serum cholesterol can be determined.

In general, cholesterol oxidase which is known for the above enzymatic method is an enzyme which oxidizes cholesterol in the presence of oxygen to form cholest-4-en-3-one and hydrogen peroxide. Thus the feature of conventional cholesterol oxidase is that one of the products formed by the reaction with cholesterol is always cholest-4-en-3-one.

The microorganisms which are known to produce such cholesterol oxidase are Nocardia spp. [Clin. Chem. vol. 19, 1350–1356 (1973)], *Brevibacterium sterolicum* [Agric. Biol. Chem. vol. 37, 2345–2350 (1973)], Streptomyces spp. [Chem. Pharm. Bull. vol. 21, 2057–2060 (1973)], and *Schizophyllum commune* [U.S. Pat. No. 4,003,794 (1977)]. It is well known that when these known cholesterol oxidases react with $\Delta^5$-$3\beta$-hydroxysteroids there are always produced $\Delta^4$-3-oxosteroids.

The present invention provides new cholesterol oxidase useful for the above explained enzymatic method for the determination of serum cholesterol. The new cholesterol oxidase according to this invention is enzymatically distinguished from known cholesterol oxidases in that the products of its reaction with $\Delta^5$-$3\beta$-hydroxysteroids are $\Delta^5$-3-oxosteroids rather than $\Delta^4$-3-oxosteroids. For example the products of the reaction of the new cholesterol oxidase with cholesterol are not cholest-4-en-3-one and hydrogen peroxide, but cholest-5-en-3-one and hydrogen peroxide.

According to this invention, the novel cholesterol oxidase is produced by cultivating a strain which belongs to the class Basidiomycetes and is capable of producing cholesterol oxidase in a culture medium and recovering the cholesterol oxidase from the culture filtrate.

A wide range of strains of the class Basidiomycetes were screened for strains productive of cholesterol oxidase. Each strain was cultivated in the usual manner in a medium (pH 5.8) containing glucose 2%, yeast extract 0.3%, polypeptone 1%, $KH_2PO_4$ 0.3% and $MgSO_4.7H_2O$ 0.1%. The culture broth was filtered and the filtrate was used as the enzyme source for the measurement of cholesterol oxidase activity. As a result thereof it has been found that the strains belonging to the genera Lentinus, Oudemansiella, Flammulina, Lepiota, Coprinus, Psilocybe, Gloeocystidium, Phellinus, Auricularia and Poria are capable of producing cholesterol oxidase according to this invention.

More particular species belonging to these genera are, for example, *Lentinus edodes* FERM-P 5776, *Oudemansiella radicate* FERM-P 5777, *Oudemansiella mucida* FERM-P 5778, *Flammulina velutipes* FERM-P 5779, *Lepiota procera* FERM-P 5780, *Coprinus comatus* FERM-P 5781, *Psilocybe coprophila* FERM-P 5782, *Gloeocystidium chrysocreas* FERM-P 5783, *Phellinus gilvus* FERM-P 5784, *Auricularia polytricha* FERM-P 5785 and *Poria epimiltina* FERM-P 5804.

All of these strains have been deposited at FERM (Fermentation Research Institute), Japan under the above indicated FERM numbers, and are open to the public and freely available.

The characteristics of these strains are as follows:

(a) *Lentinus edodes* FERM-P 5776

Cap: hemispherical or kidney-shaped, 6–10 cm in diameter. Cuticle deep brown, with overlapping tooth-marked scales and breaking up into netlike cracks. Flesh closely, tough, white and give off a smell when dry. Gills: sinuate, rather closed and white. Stipe: 3–4 cm long, 10 mm thick. Tough, lower surface out of the ring pale brown, fibrous. Upper white, smooth or striated. Spores: white in mass, cylindric to ellipsoid, size 5–7×3.5 microns.

(b) *Oudemansiella radicate* FERM-P 5777

Cap: 5–9 cm in diameter. At first bell-shaped, finally flat with a slight, central hump. Cuticle pale greyish-brown, very slimy when wet, radially wrinkled. Flesh greyish-white, thin. Gills: broad, sub-distant and adnate. Stipe: hollow, 5–12 cm long, 4–9 mm thick. Pale greyish-brown, powdery, becoming vertically striate, often twisted. Tapers towards the top, with a long tap-root, 5–30 cm long. Spores: white in mass, ellipsoid or globose, smooth, size 15–24×14–18 microns. Basidium: size 45–55×11–13 microns, with 2 or 4 spores.

(c) *Oudemansiella mucida* FERM-P 5778

Cap: 3–6 cm in diameter. Hemispherical, and thin at the margin. Shiny white and often shading to skin-colored at the center. Cuticle very slimy when wet. Powdery and shining if dry weather persists. Margin striate. Flesh white, soft, gelatinous. Gills: white, broad, sub-distant and adnate. Stipe: 3–6 cm long, 3–7 mm thick. Tough, cartilagious, white and striate above the wide membranous ring. Short, tapering upwards from the base. Spores: white in mass, ellipsoid or globose, smooth, size 20–23×16–18 microns. Basidium: size 70–100×20–30 microns, with 4 spores.

(d) *Flammulina velutipes* FERM-P 5779

Cap: at first convex, then flattened. 2–8 cm in diameter. Cuticle very slimy when wet. Yellow-ocher, with a pale color at the margin. Flesh yellowish-white, soft, thick at the center. Gills: white or pale yellow. Broad, adnexed or sinuate and rather closed. Stipe: 3–10 cm long, 2–8 mm thick. Tough, tapers downwards from apex, curved, often twisted. Dark brown, with a yellow, powdery apex, densely velvety. Flesh fibrous, finally hollow. Spores: white in mass, cylindric to ellipsoid, smooth, size 5–8×3–4 microns. Cystidium: size 33–66–×9–25 microns, with cheilocystidium and pleurocystidium.

(e) *Lepiota procera* FERM-P 5780

Cap: at first ovoid, becoming flatterned with a slight to prominent umbo. Margin thin, turned down and fringed. 10–20 cm in diameter. Cuticle uniformly brown at first, breaking up into coarse scales as the cap expands. Flesh white, soft, spongy, not very thick. Gills: white and remote. Stipe: long, thick and hollow. Tapers upwards from bulbous base. Light brown, concentrically banded with brown scales, with a thick ring near the apex. Spores: white in mass, ellipsoid, smooth, size 17–19×11–14 microns.

(f) *Coprinus comatus* FERM-P 5781

Cap: at first cylindrical then expanding below, becoming bell-shaped, margin splits as cap expands. 3–5 cm in diameter, 6–10 cm high. Cuticle, pale brown, with overlapping large shaggy woolly scales. Flesh white, thin except at the center, and fragile. Gills: free, progressively white, pale pink, black and autodigesting producing a black liquid. Stipe: 15–25 cm high, 10–15 mm thick. White and slightly fibrous with a conspicuous although soon disappearing white ring quite low down. With bulbose base. Spores: brownish-black in mass, ellipsoid, smooth, size 11–14×6–8 microns.

(g) *Psilocybe coprophila* FERM-P 5782

Cap: 2–3 cm in diameter. Hemispherical then expanded. Cuticle not slimy, umber to dark brown, not striated. With a detachable pellicle, not gelatinous. Fresh thin, umber to dark brown. Gills: broad, crowded and adnate, range 2–3 mm. At first pale color, then livid-brown. Stipe: 5–7 cm long, 3–4 cm thick. Cuticle glabrous shining, white or pale capcolor and hollow. Spores: purple-brown in mass, ellipsoid, size 6–7×3–4 microns. Cheilocystidium: spindle-shaped, size 17–20–×5–7 microns.

(h) Gloeocystidium chrysocreas FERM-P 5783

Fruit body: 4–8×2–3 cm across. All fruit bodies turn back on wood, and there are no cap. Spreading on bark, it can not peel off. Surface yellow of an egg, smooth or having nipplelike verrucae a small quantity and cracks when dry. Fresh yellowish-green, 120–300 microns thick. Margin thin and leathery. Constituent mycelium erects, range 2 microns with many sac-shaped large cells, size 15–20×6–9 microns. Sac-shaped large cells change to pink color by addition of KOH solution. Spores: white in mass, ellipsoid, smooth, size 4–5×2–3 microns.

(i) *Phellinus gilvus* FERM-P 5784

Stipe absent. Cap: half-round, overlapping each other. 5–8 cm across, 5–10 mm thick. Cuticle yellowish-brown, crowded with short, integrity hairs and fish-skined. Under surface yellowish-brown. Flesh yellowich-brown, corky. Pores: 3–5 mm long, ostioles circlet, existing 6–7 within the limits of 1 mm long. Spores: colorless, globose, smooth, size 4–5×2–3 microns. Cystidium: abundant, heavy membrane, long wedge-shaped, size 25–30×3–6 microns.

(j) *Auricularia polytricha* FERM-P 5785

Fruit body turns back on wood. Cap: ear-shaped or very irregular cup-shaped. 3–6 cm across, 2–3 cm high, approximately 10 mm thick. Upper surface brown with shoot-closed hairs, under surface pale purplish-brown. If dry weather persists, the former to reddish-brown while the later to purplish-brown, powdery and shining. But, fruit body does not shrivell practically. Flesh gelatinous, leathery and approximately 10 mm thick. Basidium: cylindric with 4 spores, size 60–70×4–5 microns. Spores: colorless, ellipsoid, curved and narrow at the base. size 8–12×3–5 microns.

(k) *Poria epimiltina* FERM-P 5804

All fruit bodies turn back on wood, and there are no cap. Flat and spreading on wood, it is difficult to peel off. 6–8 cm across. Wood is changed to deep yellowish-orange color. Yellowish-orange except the outermost color is purplish-brown. Flesh yellowish-orange. Pores: greyish and long. Ostioles are small and polygon. Pore walls thin. Spores: colorless, ellipsoid, smooth, size approximately 3.5×2 microns. cystidium absent.

The identification of these species was made by the following books: "Coloured Illustrations of Fungi of Japan" Vol. I and Vol. II, ed. by Rokuya Imazeki and Tsugio Hongo (published by Hoiku-Sha, Osaka, Japan) 1965 and "Mycological flora of Japan" ed. by Seiya Ito (published by Yoken-Do, Tokyo, Japan), vol. 2, No. 4, 1955.

Any of the strains belonging to the above mentioned genera is capable of producing cholesterol oxidase according to this invention in a medium containing or not containing cholesterol, and therefore can be used in carrying out the present invention.

In producing the cholesterol oxidase according to this invention a strain belonging to the class Basidiomycetes which is capable of producing cholesterol oxidase is cultivated aerobically in a nutrient medium in a manner well known for the cultivation of fungi of the class Basidiomycetes. The cultivation may be solid culture or liquid culture, but the latter is preferable for large scale industrial production.

As for the medium for the cultivation natural or synthetic medium containing various nutrients known per se, e.g. carbon source, nitrogen source, organic or inorganic salt, etc. may be used. The carbon source may be for example glucose, fructose, glycerol molasses, waste molasses or a variety of starch, e.g. soluble starch, corn starch, potato starch, etc. As for the sources of nitrogen, there may be used, for example, urea, yeast extract, maltose extract, peptone, corn steep liquor (CSL), soybean powder, defatted soybean, etc. As for the organic or inorganic salts there may be mentioned phosphates, sulfates, etc. of potassium, magnesium, iron, etc. If desired, other material useful for growth such as vitamins and growth promotors may be added to the culture medium. Preferably the pH of the culture medium is 4–7.

A preferred composition of the medium is, for example, soluble starch 2%, yeast extract 0.3%, polypeptone 1%, $KH_2PO_4$ 0.3% and $MgSO_4.7H_2O$ 0.1%.

Generally the cultivation is conducted at 20°–35° C. for 2–10 days under aerobic conditions. The particular conditions should of course be selected depending upon the particular strain and culture medium in order to obtain maximum production of cholesterol oxidase.

By the cultivation the cholesterol oxidase of this invention is produced and accumulated in the culture broth. After the cultivation the culture broth is subjected to filtration, centrifugal separation or the like to separate the mycellium and to obtain a filtrate containing the cholesterol oxidase. In order to recover the cholesterol oxidase from the filtrate and to purify the same there may be employed proper procedures known in the art for the isolation and purification of an enzyme, such as fractional precipitation, dialysis, adsorption-elution, chromatography, etc. or a combination of two or more of them. Thus, for example, a non-solvent such as alcohol, acetone or the like is added, in an amount of 50–80 v/v %, to the filtrate to cause precipitation of the enzyme. Alternatively or in addition thereto, salting-out may also be effected by adding a water soluble inorganic salt such as ammonium sulfate, calcium chloride, etc. to the filtrate to a concentration of 20–80 w/v %, to cause precipitation of the enzyme. The precipitate is subjected to dialysis, sephadex treatment (e.g. sephadex G-25 column) and/or ultrafiltration to obtain a crude enzyme solution. The crude solution is adsorped on a column of DEAE-sephadex A-50 previously equilibrated with 0.01 M phosphate buffer at pH 7.0. Then the elution is carried out with 0.1–0.2 M phosphate buffer at pH 7.0. The active fractions are collected and dialyzed overnight against 0.1 M acetate buffer at pH 4.0. Then the enzyme solution is again adsorbed on a column of SP-sephadex C-50 previously equilibrated with 0.01 M acetate buffer at pH 4.0 and the elution is carried out with 0.01 M acetate buffer at ph 5.0. The active fractions are collected, dialyzed against 0.01 M phosphate buffer (pH 7.0), and the dialyzed enzyme solution is concentrated with a collodion membrane and is lyophilized to obtain purified enzyme in the form of powder.

The physical and chemical properties of the enzyme (cholesterol oxidase) thus obtained in accordance with this invention are explained below by referring partly to the accompanying drawings wherein:

FIG. 1-a to FIG. 1-k are graphs showing the optimum pH of the present enzymes, FIG. 2-a to FIG. 2-k are graphs showing the optimum temperature of the present enzymes, FIG. 3-a to FIG. 3-k are graphs showing the pH stability of the present enzymes, FIG. 4-a to FIG. 4-k are graphs showing the thermostability of the present enzymes. In FIG. 1 and FIG. 3, for maintaining the pH values from 2.0 to 3.0, from 4.0 to 5.0, from 6.0 to 8.0 and from 9.0 to 10.0, there are used glycine-HCl buffer, acetate buffer, potassium phosphate buffer and borate buffer respectively.

FIG. 5-b is a pattern showing the reaction products, when the present enzyme acts on cholesterol, by high pressure liquid chromatography. FIG. 5-a is a pattern showing the authentic specimens.

In these graphs, cholesterol oxidases produced by *Lentinus edodes* FERM-P 5776, *Oudemansiella radicate* FERM-P 5777, *Oudemansiella mucida* FERM-P 5778, *Flammulina velutipes* FERM-P 5779, *Lepiota procera* FERM-P 5780, *Coprinus comatus* FERM-P 5781, *Psilocybe coprophila* FERM-P 5782, *Gloeocystidium chrysocreas* FERM-P 5783, *Phellinus gilvus* FERM-P 5784, *Auricularia polytricha* FERM-P 5785 and *Poria epimiltina* FERM-P 5804, are identified by the letters a, b, c, d, e, f, g, h, i, j and k added at the end of the Figure numbers respectively.

1. Actions and substrate specificity

Differing from the conventional cholesterol oxidases produced by Nocardia, Brevibacterium, Streptomyces and Schizophyllum, cholesterol oxidase of this invention oxidizes $\Delta^5$-3$\beta$-hydroxysteroids to form $\Delta^5$-3-oxosteroids with concomitant production of hydrogen peroxide. For example, when the enzyme of the present invention acts directly on cholesterol, cholest-5-en-3-one is produced with concomitant production of hydrogen peroxide. FIG. 5-b is a pattern showing the reaction products, when this enzyme acts on cholesterol and the products extracted with chloroform are developed by high pressure liquid chromatography. FIG. 5-a is a pattern showing the authentic specimens. Consequently, it is obvious that the reaction product, when the enzyme of the present invention acts on cholesterol, is cholest-5-en-3-one and not cholest-4-en-3-one. It is known that the conventional cholesterol oxidases catalyze both the oxidation and isomerization reactions. On the contrary, cholesterol oxidase of this invention catalyzes only the sequence of oxidation and converts cholesterol into cholest-5-en-3-one, as confirmed by comparison with the chemically synthesized material through IR, UV, melting point, optical rotation and thin layer chromatography. Hitherto, cholesterol oxidase which catalyzed only the sequence of oxidation has not been reported. Cholesterol oxidase of this invention acts only on the hydroxyl group at the 3$\beta$-position of cholesterol. A test made, for example, by decomposing the hydrogen peroxide liberated from the dehydrogenation of the 3$\beta$-position with a peroxidase, bringing the thus generated oxygen into contact with a chromogen to form a color, and measuring the absorption spectra thereof in the visible light portion of the spectrum, showed that this enzyme will act on, in addition to cholesterol among the various steroids, sterols having a hydroxyl group at the 3$\beta$-position, for example, $\beta$-cholestanol, campesterol, $\beta$-cytosterol, stigmasterol, 5$\alpha$-pregnan-3$\beta$,20$\beta$-diol, dehydroepiandrosterone, pregnenolone and ergosterol. This enzyme does not act on sterols having a hydroxyl group in other positions.

2. Optimum pH and pH stability

FIG. 1-a–FIG. 1-k are graphs showing the optimum pH of the present enzymes. The optimum pH of each of the present enzymes is near 5–7. FIG. 3-a–FIG. 3-k are graphs showing the pH stability of the present enzymes treated at each pH for 60 minutes at 37° C. The present enzymes is stable at pH 3–8, more particularly at pH 5–7.

3. Optimum temperature and thermostability

FIG. 2-a–FIG. 2-k are graphs showing the optimum temperature of the present enzymes. The optimum temperature of the present enzymes is near 40°–45° C., more particularly about 40° C. FIG. 4-a–FIG. 4-k are graphs showing the thermostability of the present enzymes, with the treatment at pH 7.0 for 10 minutes. The present enzymes is stable up to 40°–50° C.

4. Determination of enzymatic activity

The enzymatic activity is determined by measurement of the hydrogen peroxide produced by the reaction of the enzyme solution on the substrate cholesterol. The method is based on the sequence of reactions as follows: Thus cholesterol is oxidized by cholesterol oxidase to cholest-5-en-3-one with the evolution of hydrogen peroxide, which couples with 4-aminoantipyrine and phenol in the presence of peroxidase to yield a quinoneimine dye with maximum absorption at 500 nm. To conduct this reaction there is used a reaction mixture, in a final volume of 3.0 ml, composed of 0.1 ml of the enzyme solution, 2 μmoles of cholesterol in 0.1 ml of ethanol, 250 μmoles of phosphate buffer, pH 7.0, 2.46 μmoles of 4-aminoantipyrine, 42 μmoles of phenol, and 24 units of peroxidase obtained from horseradish. The reaction is carried out at 37° C. for 10 minutes with shaking. One unit of cholesterol oxidase activity was defined as the amount of the enzyme which catalyzes the oxidation of 1 μmole of cholesterol per minute at 37° C.

5. Effect of inhibitors etc.

The activity of the present enzymes is markedly inhibited by $Cu^{2+}$ and $Hg^{2+}$. Inhibition caused by these metal ions is almost completely prevented by the addition of glutathione. $Ca^{2+}$, $Ba^{2+}$, $Co^{2+}$, $Ni^{2+}$, $Mg^{2+}$, $Mn^{2+}$, and $Fe^{2+}$ do not inhibit the enzyme activity. The addition of detergents, for example, 0.01% of Triton X-100, inhibit almost completely the enzymes activity. Various metal chelating agents such as EDTA, o-phenanthroline, $\alpha,\alpha'$-dipyridyl and $\beta$-hydroxyquinoline are not inhibitory.

6. Molecular weight

The molecular weight of the present enzymes is determined by gel filtration on Sephadex G-150. The molecular weight of the present enzymes are estimated to be about 58000–62000, except that the molecular weight of cholesterol oxidase produced by *Phellinus gilvus* FERM-P 5784 is about 85000.

The invention will be further explained by means of the following Examples which are given for illustrative purpose only and not for limiting the scope of the invention.

EXAMPLE 1

The incubation was conducted by charging 100 ml of a seed culture medium containing 2% glucose, 0.3% yeast extract, 0.3% polypeptone, 0.1% $KH_2PO_4$, and 0.05% $MgSO_4.7H_2O$, of 500 ml Erlenmeyer flasks. The flasks were stopped with cotton, sterilized for 20 minutes at 120° C. After cooling, the medium was inoculated in a conventional manner with the strain of *Lentinus edodes* FERM-P 5776, which had been cultivated separately in a slant culture medium containing 3% glucose, 0.5% Ebios and 1.5% agar. After 7 days shaking incubation at 27° C., the contents of the flasks were used for the subsequent incubation. Fifteen liters of a liquid culture medium containing 2% glucose, 0.3% yeast extract, 1% polypeptone, 0.3% $KH_2PO_4$, 0.1% $MgSO_4.7H_2O$, and 0.5% soybean oil, in 30 liters stainless steel jar fermenter were sterilized at 120° C. for 20 minutes and cooled. Then, the content of the flasks obtained above was inoculated in the culture medium in said jar fermenter. The medium was subjected to aerobic incubation with stirring (200 r.p.m.) for 6 days at 27° C., at an aeration rate of 0.6 liter/liter/minute.

Thereafter, the culture broth thus obtained was filtered using a filter press. This culture filtrate showed a cholesterol oxidase activity of 0.05 units per ml. To the filtrate (13 liters), ammonium sulfate was added at 5° C. until 80% saturation. The precipitate formed was subjected to dialysis against 0.01 M phosphate buffer at pH 7.0, and furthermore, the dialyzed enzyme solution was applied on DEAE Sephadex A-50 column which had been previously equilibrated with 0.01 M phosphate buffer at pH 7.0. Elution was carried out with 0.2 M phosphate buffer at pH 7.0, and the active fractions were collected, dialyzed overnight against 0.001 M phosphate buffer at pH 7.0 and lyophilized. The lyophilized preparation (1.5 g) thus obtained showed a specific activity of cholesterol oxidase of 0.15 units per mg.

EXAMPLE 2

In the same manner as in Example 1, *Oudemansiella radicate* FERM-P 5777 was cultivated to obtain a culture filtrate showing a cholesterol oxidase activity of 1.10 unit per ml. The culture filtrate was then processed as in Example 1 to obtain a lyophilized preparation. The lyophilized preparation (2.0 g) showed a specific activity of cholesterol oxidase of 0.28 unit per mg.

EXAMPLE 3

The procedure of Example 1 was repeated except that *Oudemansiella mucida* FERM-P 5778 was cultivated in the main medium composed of soluble starch 2%, yeast extract 0.3%, polypeptone 1%, $KH_2PO_4$ 0.3% and $MgSO_4.7H_2O$ 0.1% and soybean oil 0.5% to obtain a culture filtrate showing a cholesterol oxidase activity of 0.11 units per ml. The culture filtrate was processed as in Example 1 to obtain a lyophilized preparation (1.0 g) showing a specific activity of cholesterol oxidase of 0.60 units per mg.

EXAMPLE 4

In the same manner as in Example 1, *Flammulina velutipes* FERM-P 5779 was cultivated to obtain a culture filtrate showing a cholesterol oxidase activity of 0.10 units per ml. Then the filtrate was processed as in Example 1 to obtain a lyophilized preparation (1.5 g) having a specific activity of cholesterol oxidase of 0.50 units per mg.

EXAMPLE 5

The procedure of Example 1 was repeated except that *Lepiota procera* FERM-P 5780 was cultivated for 7 days, to obtain a culture filtrate showing a cholesterol oxidase activity of 0.05 units per ml. The filtrate was processed as in Example 1 to obtain a lyophilized preparation (2.5 g) having a specific activity of cholesterol oxidase of 0.12 units per mg.

EXAMPLE 6

The procedure of Example 3 was repeated except that *Coprinus comatus* FERM-P 5781 was cultivated for 5 days, to obtain a culture filtrate showing a cholesterol oxidase activity of 0.10 units per ml. The filtrate was processed as in Example 1 to obtain a lyophilized preparation (1.0 g) having a specific activity of cholesterol oxidase of 0.40 units per mg.

EXAMPLE 7

The procedure of Example 3 was repeated except that *Psilocybe coprophila* FERM-P 5782 was cultivated for 5 days, to obtain a culture filtrate showing a cholesterol oxidase activity of 0.10 units per ml. The filtrate was processed as in Example 1 to obtain a lyophilized preparation (1.5 g) having a specific activity of cholesterol oxidase of 0.50 units per mg.

EXAMPLE 8

The procedure of Example 3 was repeated except that *Gloeocystidium chrysocreas* FERM-P 5783 was cultivated for 4 days, to obtain a culture filtrate showing a cholesterol oxidase activity of 1.3 units per ml. The filtrate was processed as in Example 1 to obtain a lyophilized preparation (1.5 g) having a specific activity of cholesterol oxidase of 6.0 units per mg.

EXAMPLE 9

The procedure of Example 1 was repeated except that *Phellinus gilvus* FERM-P 5784 was cultivated for 4 days, to obtain a filtrate showing a cholesterol oxidase activity of 0.20 units per ml. The filtrate was processed as in Example 1 to obtain a lyophilized preparation (2.0 g) having a specific activity of cholesterol oxidase of 1.0 unit per mg.

EXAMPLE 10

The procedure of Example 3 was repeated except that *Auricularia polytricha* FERM-P 5785 was cultivated for 5 days, to obtain a culture filtrate showing a cholesterol oxidase activity of 0.10 units per ml. The filtrate was processed as in Example 1 to obtain a lyophilized preparation (2.0 g) having a specific activity of cholesterol oxidase of 0.52 units per mg.

EXAMPLE 11

The procedure of Example 3 was repeated except that *Poria epimiltina* FERM-P 5804 was cultivated in the main medium for 6 days, to obtain a culture filtrate showing a cholesterol oxidase activity of 0.16 units per ml. The filtrate was processed as in Example 1 to obtain a lyophilized preparation (1.5 g) having a specific activity of cholesterol oxidase of 0.45 units per mg.

What we claim is:

1. A process for producing a cholesterol oxidase which comprises cultivating a strain belonging to the class Basidiomycetes which is capable of producing cholesterol oxidase in a culture medium to accumulate the cholesterol oxidase, and recovering the cholesterol oxidase from the resulting culture broth, said strain belonging to a genus selected from the group consisting of Lentinus, Oudemansiella, Flammulina, Lepiota, Coprinus, Psilocybe, Gloeocystidium, Phellinus, Auricularia, and Poria, said cholesterol oxidase being characterized by activity to oxidase cholesterol in the presence of oxygen to form cholest-5-en-3-one and hydrogen peroxide.

2. A process according to claim 1 wherein there is used a strain belonging to the genus Lentinus.

3. A process according to claim 1 wherein there is used a strain belonging to the genus Oudemansiella.

4. A process according to claim 1 wherein there is used a strain belonging to the genus Flammulina.

5. A process according to claim 1 wherein there is used a strain belonging to the genus Lepiota.

6. A process according to claim 1 wherein there is used a strain belonging to the genus Coprinus.

7. A process according to claim 1 wherein there is used a strain belonging to the genus Psilocybe.

8. A process according to claim 1 wherein there is used a strain belonging to the genus Gloeocystidium.

9. A process according to claim 1 wherein there is used a strain belonging to the genus Phellinus.

10. A process according to claim 1 wherein there is used a strain belonging to the genus Auricularia.

11. A process according to claim 1 wherein there is used a strain belonging to the genus Poria.

12. A process according to claim 1 wherein there is used a strain selected from the group consisting of *Lentinus edodes* FERM-P 5776, *Oudemansiella radicate* FERM-P 5777, *Oudemansiella mucida* FERM-P 5778, *Flammulina velutipes* FERM-P 5779, *Lepiota procera* FERM-P 5780, *Coprinus comatus* FERM-P 5781, *Psilocybe coprophila* FERM-P 5782, *Gloeocystidium chrysocreas* FERM-P 5783, *Phellinus gilvus* FERM-P 5784, *Auricularia polytricha* FERM-P 5785 and *Poria epimiltina* FERM-P 5804.

13. A cholesterol oxidase produced by a strain of the class Basidiomycetes which is characterized by activity to oxidize cholesterol in the presence of oxygen to form cholest-5-en-3-one and hydrogen peroxide, said strain belonging to a genus selected from the group consisting of Lentinus, Oudemansiella, Flammulina, Lepiota, Coprinus, Psilocybe, Gloeocystidium, Phellinus, Auricularia, and Poria.

* * * * *